United States Patent [19]

Leichnitz

[11] 4,277,251

[45] Jul. 7, 1981

[54] METHOD AND DEVICE FOR DETERMINING THE ALCOHOL CONTENT OF A PERSON'S BREATHING

[75] Inventor: Kurt Leichnitz, Gross Gronau, Fed. Rep. of Germany

[73] Assignee: Drägerwerk Aktiengesellschaft, Fed. Rep. of Germany

[21] Appl. No.: 121,888

[22] Filed: Feb. 15, 1980

[30] Foreign Application Priority Data

Mar. 19, 1979 [DE] Fed. Rep. of Germany ....... 2910778

[51] Int. Cl.³ .................... G01N 27/62; G01N 1/22
[52] U.S. Cl. .................... 23/232 R; 422/59; 422/85; 422/84; 422/88; 23/907
[58] Field of Search ............. 23/232 R, 232 C, 232 E, 23/907; 422/59, 83, 84, 85, 86, 88, 92, 89; 73/23, 23.1; 128/719

[56] References Cited

U.S. PATENT DOCUMENTS

| | | | |
|---|---|---|---|
| 2,826,908 | 3/1958 | Skarstrom | 422/89 |
| 3,305,000 | 2/1967 | Bullen et al. | 23/232 C |
| 3,522,009 | 7/1970 | Borkenstein | 422/85 |
| 3,697,418 | 10/1972 | Johnson | 210/22 |
| 3,734,692 | 5/1973 | Lucker et al. | 422/85 |
| 3,746,512 | 7/1973 | Kamei et al. | 422/84 |

FOREIGN PATENT DOCUMENTS 534680 6/1975 U.S.S.R. .................... 422/84

Primary Examiner—William F. Smith
Assistant Examiner—Chris Konkol
Attorney, Agent, or Firm—McGlew and Tuttle

[57] ABSTRACT

A method of determining the alcohol content of air exhaled by a person using a flow through testing tube having an alcohol indicating material therein and a sampling tube to which the air is directed which has a material therein for retaining the alcohol of the breathing air and also using a suction pump comprises cooling the sampling tube, passing the exhaled air through the cooled sampling tube, measuring a volume of the air passing through the cooled sampling tube, heating the sampling tube and connecting the suction pump to the sampling tube to suck flushing air through the heated tube and then through the testing tube. The sampling tube advantageously contains a silica gel to retain the alcohol therein. The volume measuring device may be a measuring bag.

1 Claim, 2 Drawing Figures

METHOD AND DEVICE FOR DETERMINING THE ALCOHOL CONTENT OF A PERSON'S BREATHING

FIELD AND BACKGROUND OF THE INVENTION

This invention relates in general to breath testing devices and in particular to a new and useful apparatus and method for determining the alcohol content of exhaled air.

Breath alcohol testers must be easy to carry by the user and be able to be applied immediately. The test result should be sufficiently accurate, despite the often adverse circumstances under which the test must be performed, also in the open. The often lacking willingness of the test person to cooperate must not affect the test result.

In one known breath alcohol tester the test person blows directly through a test tube via a mouthpiece. The parameter "exhaled amount of gas", required to determine the alcohol concentration in the exhaled air, is found by means of a measuring bag which follows the test tube and must be inflated. This known method required test tubes of low resistance to keep the blowing effort of the test person within limits. Therefore, the breath alcohol test tubes must be of relatively large section and can have a relatively short preparation layer only. Since the length of discoloration of the reagent preparation is the measure of the alcohol content in the exhaled air, a prolongation would be in the sense of a greater measuring sensitivity, (DE-PS No. 10 52 630).

One known device to measure the exhaled gas mixture by means of a breath alcohol test tube has a breath sampling chamber of a defined maximum volume. It is brought, by the breath blown in, from a starting position into an end position so that it contains a breath sample of a defined volume. When the breath sampling chamber is filled, a pump is actuated which conducts the breath contained in the breath sampling chamber to and through the breath alcohol test tube via a line. Conducting the breath through the breath sampling chamber leads to difficulties on account of cooling. To prevent this, the entire device, not only the chamber but also all lines, is heated. This makes the device complicated, bulky and, fundamentally, requires the warm-up period before use (DE-PS No. 12 98 311).

The length of discoloration being the measure of the alcohol content in the exhaled air, lengthening it would produce a greater measuring sensitivity. The test tube employed to analyze the air at work stations are used in conjunction with a gas sensing pump. With it, greater flow resistances in the test tube can be overcome. These standard test tubes are of smaller diameter, from which then follows a longer reagent length, which is totally in the sense of the desired extension of the discoloration.

SUMMARY OF THE INVENTION

The invention provides a breath alcohol test method and device using alcohol test tubes, which requires no blow effort from the test person and yet furnishes sufficiently accurate test results.

In accordance with the invention exhaled air is directed through a tube which is placed in a cooler and the alcohol content of the air is retained in a silica gel contained in the tube. The air is directed into a volume measuring device. Thereafter the sampling tube is heated and a flushing air is directed through the sampling tube and the silica gel therein and into an alcohol test tube.

This makes it possible in an advantageously simple manner, using alcohol test tubes, to carry out exact, quantitative breath alcohol analyses without overstressing the test person by too great a test tube resistance. With a cooled sampling tube of little resistance the alcohol is stored in a first step without exertion on the part of the test person and, independently thereof, the alcohol content is then determined in a second step from the heated sampling tube by means of a gas sensing pump and a standard test tube. The method presents no problems in its execution because, except for some connectors, no components other than the known ones are required.

Accordingly it is an object of the invention to provide a method of determining the alcohol content of air exhaled by a person using a flow through testing tube having an alcohol indicating material therein and also a sampling tube to which the air is directed which has a material therein for retaining the alcohol of the breathing air, comprising cooling the sampling tube as the exhaled air is directed through the sampling tube and into a measuring device until a predetermined quantity of air has been collected, thereafter heating the sampling tube and passing a flushing air through the tube and through the alcohol testing tube in order to obtain an indication of the alcohol present therein.

A further object of the invention is to provide a device for testing a person's breath for the presence of alcohol which comprises a sampling tube having silica gel therein which is connectable to a measuring device for the passage of a predetermined quantity of air therethrough while the tube is being cooled and which also includes heater means for heating the tube after a selected volume of breathing air is passed therethrough so as to flush the alcohol from the material retaining the alcohol in the tube into an alcohol testing tube to indicate the alcohol present.

A further object of the invention is to provide a device for determining alcohol content of a person's exhaled air which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
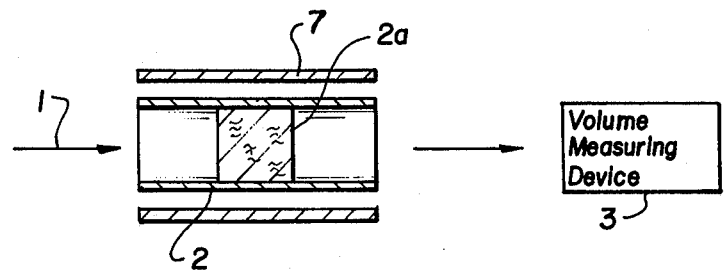
FIG. 1 is a schematic sectional view of a sampling tube and volume measuring device for use in obtaining a sample of exhaled air.

Referring to the drawings in particular, the invention embodied therein comprises an apparatus and method for testing for alcohol content in exhaled air 1 which is directed in a first step through a sampling tube 2 which is arranged in a cooler so that it is cooled. In addition, the sampling tube contains a silica gel 2a which retains alcohol of the exhaled air. The exhaled air 1 is directed through the tube 2 in a quantity to produce a predetermined volume which is measured by a volume measuring device 3.

After the initial volume is obtained, flushing air is directed through the tube 2 when the tube is being heated in a heater 8. This flushing air passes through the silica gel 2a and through an alcohol test tube 4 where the alcohol is indicated.

The method according to the invention is shown schematically in the drawing.

Figure 2:
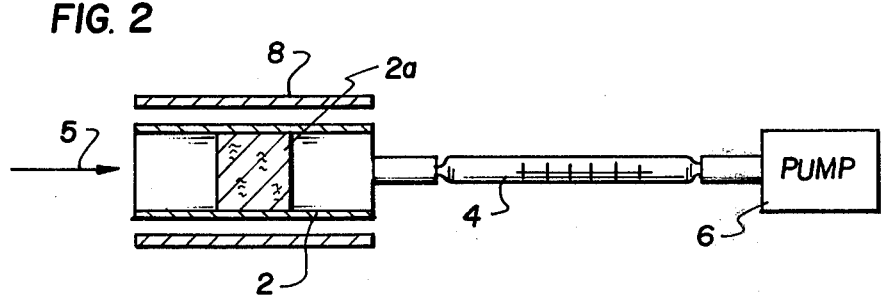
FIG. 2 is a view similar to FIG. 1 showing the sampling tube position in which it is used for directing the flushing air through the alcohol retaining material and into an alcohol testing tube.

It shows these steps:
1. Sampling according to FIG. 1.
2. Analysis according to FIG. 2.

Within the scope of sampling per step 1, the exhaled air 1 to be tested for alcohol is blown by lung power at arbitrary velocity through a sampling tube 2 which is filled with silica gel 2a and cooled by a cooler 7 to about 0° to 5° C., and the amount of exhaled air blown through it is determined in the process in a succeeding volume measuring device 3. The flow resistance of the sampling tube 2 is low. While the exhaled air flows through it, the alcohol content is retained in the sampling tube filling 2a.

After sampling is concluded and after the respective exhaled volume has moved through the sampling tube 2, the tube is removed from the cooler 7 and, as step 2, exposed to a heater 8 while being attached at the same time to an alcohol test tube 4 having a material therein which indicates alcohol present and relative amount. This involves a standard test tube to be used with a gas sensing pump.

The measurement starts at a temperature of 150° to 200° C. in the sampling tube 2. Flushing air 5 is sucked by the gas sensing pump 6 first through the sampling tube 2 and then through the alcohol test tube 4 for this purpose. The discoloration in the alcohol test tube 4 is the measure of the alcohol content in the exhaled air.

While specific embodiments of the invention have been shown and described in detail to illustrate the application of the principles of the invention, it will be understood that the invention may be embodied otherwise without departing from such principles.

What is claimed is:

1. A method of determining the alcohol content of air, exhaled by a person, of the type in which a flow of the exhaled air is passed through a sample tube which has a silica gel therein for retaining the alcohol in the air, comprising cooling the sample tube and silica gel to a temperature of 0° to 5° C., directing exhaled air through the cooled tube and the alcohol retaining silica gel while measuring the air which passes through the sample tube to obtain a predetermined volume, and subsequently heating the sample tube and silica gel to a temperature of 150° to 200° C., and then directing a flushing air therethrough at a temperature of 150° to 200° C.

* * * * *